(12) United States Patent
Regan et al.

(10) Patent No.: US 10,874,370 B2
(45) Date of Patent: Dec. 29, 2020

(54) PULSE MEASUREMENT IN OPTICAL IMAGING

(71) Applicant: Open Water Internet Inc., San Francisco, CA (US)

(72) Inventors: Caitlin Regan, Sausalito, CA (US); Sarmishtha Satpathy, San Francisco, CA (US); Edgar Emilio Morales Delgado, San Francisco, CA (US); Craig Newswanger, Oakland, CA (US)

(73) Assignee: Open Water Internet Inc., San Francisco, CA (US)

( * ) Notice: Subject to any disclaimer, the term of this patent is extended or adjusted under 35 U.S.C. 154(b) by 0 days.

(21) Appl. No.: 16/260,015

(22) Filed: Jan. 28, 2019

(65) Prior Publication Data

US 2020/0241151 A1 Jul. 30, 2020

(51) Int. Cl.
*A61B 6/00* (2006.01)
*A61B 5/00* (2006.01)
(Continued)

(52) U.S. Cl.
CPC .......... *A61B 6/5247* (2013.01); *A61B 5/0015* (2013.01); *A61B 5/0026* (2013.01);
(Continued)

(58) Field of Classification Search
CPC ... H03C 1/00; H03C 1/02; H03C 1/46; H03C 3/36; H03C 3/38; H03C 3/40; H03C 2200/0058; G01T 1/00; G01T 1/15; G01T 1/16; G01T 1/1603; G01T 1/1606; G01T 1/161; G01T 1/17; G01T 1/172; G01T 1/24; G01T 1/241; G01T 1/244; G01T 1/29; G01T 1/2907; G01T 1/2914; G01T 1/2921; G01T 1/2928; G01T 1/2935; G01T 1/2985; G01T 1/36; G01T 1/361; G01T 1/366; H04N 5/30; H04N 5/32; H04N 5/3205; H04N 5/33; H04N 5/335; G06T 5/50; G06T 7/0012; G06T 7/0014; G06T 2207/00; G06T 2207/10; G06T 2207/10028; G06T 2207/10048; G06T 2207/10072;
(Continued)

(56) References Cited

U.S. PATENT DOCUMENTS 6,172,760 B1 1/2001 Son
6,956,650 B2 10/2005 Boas
(Continued)

OTHER PUBLICATIONS

Arridge et al. Nonuniqueness in diffusion-based optical tomography, Optics Letters, Jun. 1, 1998, vol. 23, No. 11, pp. 882-884.
(Continued)

*Primary Examiner* — Anastasia Midkiff
(74) *Attorney, Agent, or Firm* — Freestone Intellectual Property Law PLLC; Aaron J. Visbeek

(57) ABSTRACT

A light pulse is emitted from a light source for illuminating a medium. Energy level data of the light pulse is measured before the light pulse enters the medium. An image sensor captures an image that includes an interference pattern generated by an exit signal of the light pulse exiting the medium interfering with a reference wavefront. Normalized intensity data is generated by normalizing intensity data exit signal data by the energy level data.

20 Claims, 12 Drawing Sheets

(51) Int. Cl.
    *G01T 1/161* (2006.01)
    *H03C 3/40* (2006.01)
    *G01T 1/16* (2006.01)
    *G01T 1/29* (2006.01)
(52) U.S. Cl.
    CPC .......... *A61B 5/0033* (2013.01); *A61B 5/0059* (2013.01); *A61B 5/7235* (2013.01); *A61B 5/7278* (2013.01); *A61B 6/501* (2013.01); *A61B 5/0013* (2013.01); *A61B 5/0017* (2013.01); *A61B 5/0097* (2013.01); *A61B 5/6814* (2013.01); *A61B 2562/0233* (2013.01); *A61B 2562/0242* (2013.01); *A61B 2562/146* (2013.01); *A61B 2576/026* (2013.01); *G01T 1/16* (2013.01); *G01T 1/161* (2013.01); *G01T 1/2914* (2013.01); *G06T 2207/10101* (2013.01); *H03C 3/40* (2013.01)
(58) Field of Classification Search
    CPC . G06T 2207/10076; G06 2207/10084; G06T 2207/10101; G06T 2207/10116; G06T 2207/10132; G06T 2207/10136; G06T 2207/20068; G06T 2207/20212; G06T 2207/30016; A61B 5/00; A61B 5/0002; A61B 5/0004; A61B 5/0013; A61B 5/0015; A61B 5/0017; A61B 5/002; A61B 5/0024; A61B 5/0026; A61B 5/0028; A61B 5/0033; A61B 5/0035; A61B 5/004; A61B 5/0042; A61B 5/0048; A61B 5/0051; A61B 5/0059; A61B 5/065; A61B 5/066; A61B 5/0077; A61B 5/0082; A61B 5/0093; A61B 5/0097; A61B 5/68; A61B 5/6801; A61B 5/6803; A61B 5/6813; A61B 5/6814; A61B 5/72; A61B 5/7203; A61B 5/7207; A61B 5/7214; A61B 5/7228; A61B 5/7235; A61B 5/7278; A61B 5/7285; A61B 6/4417; A61B 6/501; A61B 6/52; A61B 6/5211; A61B 6/5229; A61B 6/5247; A61B 18/20; A61B 18/203; A61B 18/22; A61B 2018/00773; A61B 2018/00779; A61B 2018/00869; A61B 2018/00875; A61B 2018/2035; A61B 2018/20357; A61B 2018/2065; A61B 2018/208; A61B 2018/22333; A61B 2018/2255; A61B 2560/00; A61B 2560/02; A61B 2560/04; A61B 2562/00; A61B 2562/0233; A61B 2562/0238; A61B 2562/0242; A61B 2562/04; A61B 2562/06; A61B 2562/14; A61B 2562/146; A61B 2562/16; A61B 2562/185; A61B 2576/00; A61B 2576/02; A61B 2576/026
    See application file for complete search history.

(56) References Cited

U.S. PATENT DOCUMENTS

| | | |
|---|---|---|
| 7,119,906 B2 | 10/2006 | Pepper |
| 7,460,248 B2 | 12/2008 | Kurtz |
| 7,551,809 B2 | 6/2009 | Taira |
| 7,610,082 B2 | 10/2009 | Chance |
| 7,647,091 B2 | 1/2010 | Ntziachristos |
| 7,728,986 B2 | 6/2010 | Lasker |
| 7,804,070 B1 | 9/2010 | Pan |
| 7,821,640 B2 | 10/2010 | Koenig |
| 7,822,468 B2 | 10/2010 | Stammes |
| 7,826,878 B2 | 11/2010 | Alfano |
| 7,898,649 B2 | 3/2011 | Masumura |
| 7,965,389 B2 | 6/2011 | Da Silva |
| 7,983,740 B2 | 7/2011 | Culver |
| 7,928,896 B2 | 8/2011 | Jin |
| 8,014,847 B2 | 9/2011 | Shastri |
| 8,120,784 B2 | 2/2012 | Da Silva |
| 8,170,651 B2 | 5/2012 | Lorenzo |
| 8,239,006 B2 | 8/2012 | Zhu |
| 8,263,947 B2 | 9/2012 | Da Silva |
| 8,289,502 B2 | 10/2012 | Yoshida |
| 8,326,567 B2 | 12/2012 | Masumura |
| 8,330,642 B2 | 12/2012 | Jin |
| 8,355,131 B2 | 1/2013 | Bakker |
| 8,357,915 B2 | 1/2013 | Guyon |
| 8,374,409 B2 | 2/2013 | Jochemsen |
| 8,416,421 B2 | 4/2013 | Wang |
| 8,450,674 B2 | 5/2013 | Yang |
| 8,451,450 B2 | 5/2013 | Heng |
| 8,520,921 B2 | 8/2013 | Ziegler |
| 8,525,998 B2 | 9/2013 | Yaqoob |
| 8,527,242 B2 | 9/2013 | Granot |
| 8,531,662 B2 | 9/2013 | Van Der Mark |
| 8,563,932 B2 | 10/2013 | Fang |
| 8,634,077 B2 | 1/2014 | Hu |
| 8,649,015 B2 | 2/2014 | Ichihara |
| 8,917,442 B2 | 3/2014 | Baym |
| 8,717,574 B2 | 5/2014 | Yang |
| 8,814,795 B2 | 8/2014 | Derode |
| 8,817,255 B2 | 8/2014 | Masumura |
| 8,830,573 B2 | 9/2014 | Cui |
| 8,847,175 B2 | 9/2014 | Laidevant |
| 8,937,284 B2 | 1/2015 | Fang |
| 8,954,130 B2 | 2/2015 | Masumura |
| 8,976,433 B2 | 3/2015 | Masumura |
| 9,012,869 B2 | 4/2015 | Andersson-Engels |
| 9,036,970 B2 | 5/2015 | Guyon |
| 9,037,216 B2 | 5/2015 | Hielscher |
| 9,057,695 B2 | 6/2015 | Masumura |
| 9,131,851 B2 | 9/2015 | Fukutani |
| 9,134,229 B2 | 9/2015 | Lesage |
| 9,179,842 B2 | 11/2015 | Nakaji |
| 9,207,171 B2 | 12/2015 | Nadakuditi |
| 9,234,841 B2 | 1/2016 | Wang |
| 9,282,932 B2 | 3/2016 | Kudo |
| 9,297,752 B2 | 3/2016 | Shimokawa |
| 9,304,490 B2 | 4/2016 | Masumura |
| 9,313,423 B2 | 4/2016 | Wang |
| 9,335,604 B2 | 5/2016 | Popovich |
| 9,335,605 B2 | 5/2016 | Wang |
| 9,341,569 B2 | 5/2016 | 'T Hooft |
| 9,354,166 B2 | 5/2016 | Judkewitz |
| 9,373,020 B2 | 6/2016 | Kudo |
| 9,407,796 B2 | 8/2016 | Dinten |
| 9,427,213 B2 | 8/2016 | Suzuki |
| 9,480,425 B2 | 11/2016 | Culver |
| 9,486,142 B2 | 11/2016 | Hielscher |
| 9,488,574 B2 | 11/2016 | Koehler |
| 9,509,956 B2 | 11/2016 | Piestun |
| 9,622,663 B2 | 4/2017 | Fang |
| 9,689,797 B2 | 6/2017 | Sun |
| 9,724,489 B2 | 8/2017 | Barbour |
| 9,730,649 B1 | 8/2017 | Jepsen |
| 9,750,413 B2 | 9/2017 | Sandusky |
| 10,016,137 B1* | 7/2018 | Yang .................... H04N 5/2256 |
| 2003/0139667 A1* | 7/2003 | Hewko ................ A61B 5/0059 600/410 |
| 2010/0016732 A1 | 1/2010 | Wells |
| 2012/0070817 A1 | 3/2012 | Yang |
| 2014/0081096 A1 | 3/2014 | Baym |
| 2014/0114181 A1 | 4/2014 | Wu |
| 2014/0303473 A1 | 10/2014 | Nanaumi |
| 2015/0101411 A1* | 4/2015 | Zalev ................. G01N 29/2418 73/643 |
| 2015/0182121 A1 | 7/2015 | Barbour |
| 2015/0238092 A1 | 8/2015 | Masumura |
| 2015/0241342 A1 | 8/2015 | Zhou |
| 2015/0346027 A1 | 12/2015 | Khare |
| 2015/0351635 A1 | 12/2015 | Cerussi |
| 2016/0081556 A1* | 3/2016 | Dreher ..................... A61B 3/10 600/319 |
| 2016/0085135 A1 | 3/2016 | Park |

(56) References Cited

U.S. PATENT DOCUMENTS

| | | |
|---|---|---|
| 2016/0157723 A1 | 6/2016 | Kanick |
| 2016/0198954 A1* | 7/2016 | Wang .................. A61B 5/0095 600/407 |
| 2016/0262723 A1 | 9/2016 | Zhu |
| 2016/0363527 A1 | 12/2016 | Ruan |
| 2017/0118423 A1 | 4/2017 | Zhou |
| 2017/0163946 A1 | 6/2017 | Komanduri |
| 2017/0168565 A1 | 6/2017 | Cohen |
| 2017/0202633 A1 | 7/2017 | Liu |
| 2017/0230555 A1 | 8/2017 | Tabirian |
| 2017/0231501 A1 | 8/2017 | Culver |

OTHER PUBLICATIONS

Hofmann et al. Differential light detector, Rev. Sci. Instrum, Feb. 1979, vol. 50, No. 2, paes 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

\* cited by examiner

PULSE MEASUREMENT IN OPTICAL IMAGING

TECHNICAL FIELD

This application is related to optical imaging and in particular to measuring a pulse for optical imaging.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, improve accuracy, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
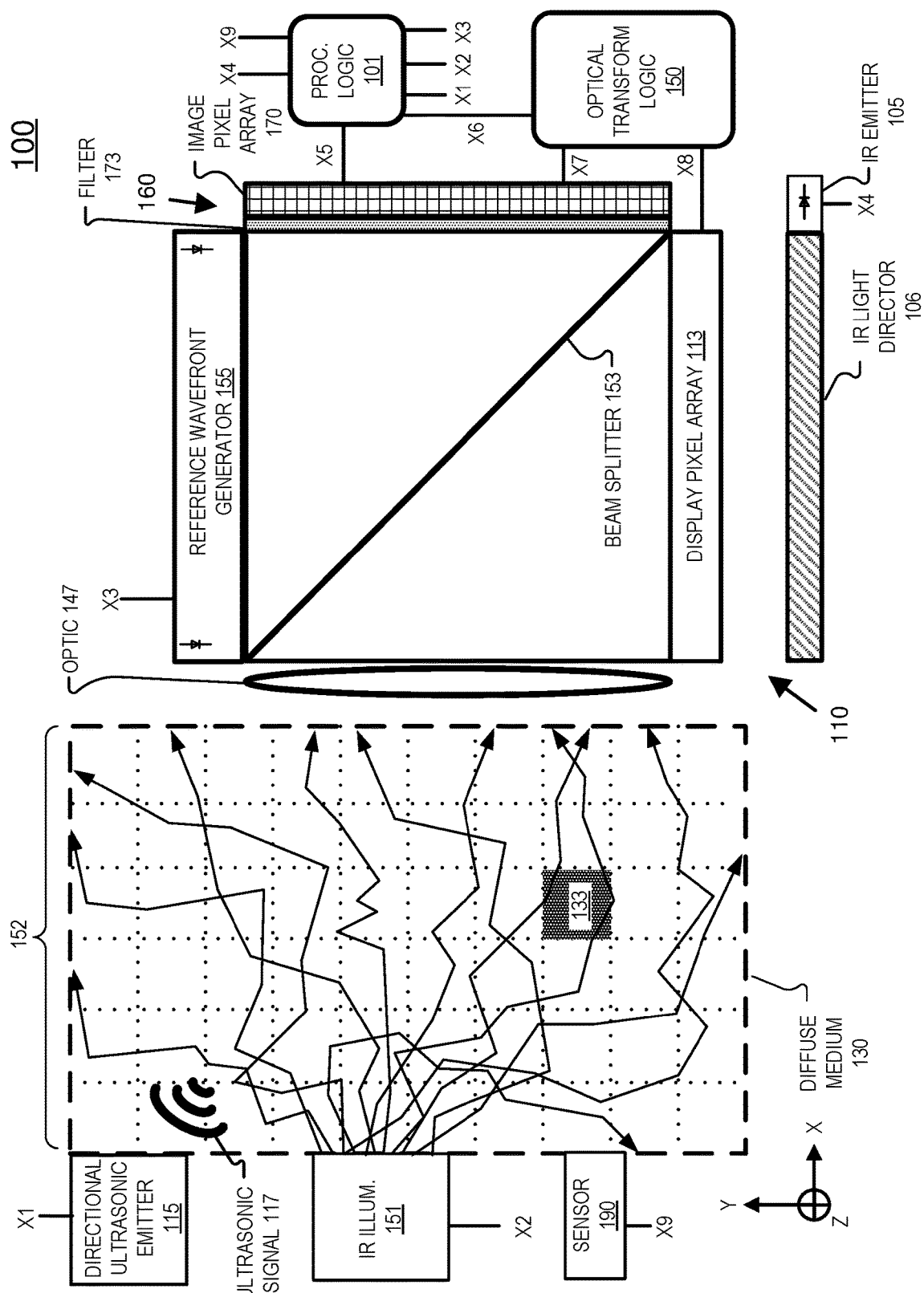
FIGS. 1A-1C illustrate an example imaging system that includes a display pixel array, an image pixel array, and a beam splitter, in accordance with an embodiment of the disclosure.

Embodiments of a system, device, and method for optical imaging with pulse measurement are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light and to at least some wavelengths of visible light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue and other diffuse mediums with visible light and near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least scattered (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is received at the detector. Thus, efficacy and power limitations as well as safety limits on input intensity limit TOF imaging resolution, depth and utility.

In contrast to TOF imaging, some embodiments of the disclosure may illuminate a diffuse medium with an infrared light or visible light while an ultrasound emitter is focused on a particular voxel. The light used to illuminate the diffuse medium may be a light pulsed generated by a pulsed light source such as a pulsed laser, for example. Continuous wave lasers may also be used, in some embodiments. Laser light pulses may be emitted from a laser at a particular frequency such as between 300 Hz. and 1000 Hz. However, the laser light pulses emitted by the laser are not exactly the same and may have significant differences in intensity, duration, or beam shape. Hence, the laser light pulses that illuminate the medium or tissue have varying power.

In an example imaging system of the disclosure, a light pulse illuminates a medium while an ultrasound emitter is focused on a particular voxel. An energy meter measures an energy level data of the light pulse before it enters the medium for normalization purposes. A portion of the light pulse encountering the particular voxel may be wavelength-shifted by the ultrasonic signal into a wavelength-shifted exit signal. The wavelength-shifted exit signal is the portion of the light pulse that is reflected from and/or transmitted through the voxel (while the ultrasonic emitter is focused on the voxel). The wavelength-shifted exit signal is interfered with a reference beam to generate an interference pattern that is captured by an image sensor. Intensity data is generated from the image of the interference pattern and that intensity is normalized according to the energy level data captured by the energy meter. The intensity data may be used as a voxel value in a composite image of the medium. Since there may be significant variance in the energy of each laser pulse that is used to illuminate the medium while different voxels are being imaged, measuring the energy level of the laser pulses that are used to illuminate the different voxels allows for a more accurate composite image. These embodiments and others will be described in more detail with references to FIGS. 1A-7.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise. For the purposes of the disclosure, visible light has a wavelength from approximately 400 nm to 700 nm and near-infrared light has a wavelength from approximately 700 nm to 1400 nm.

Figure 1B:
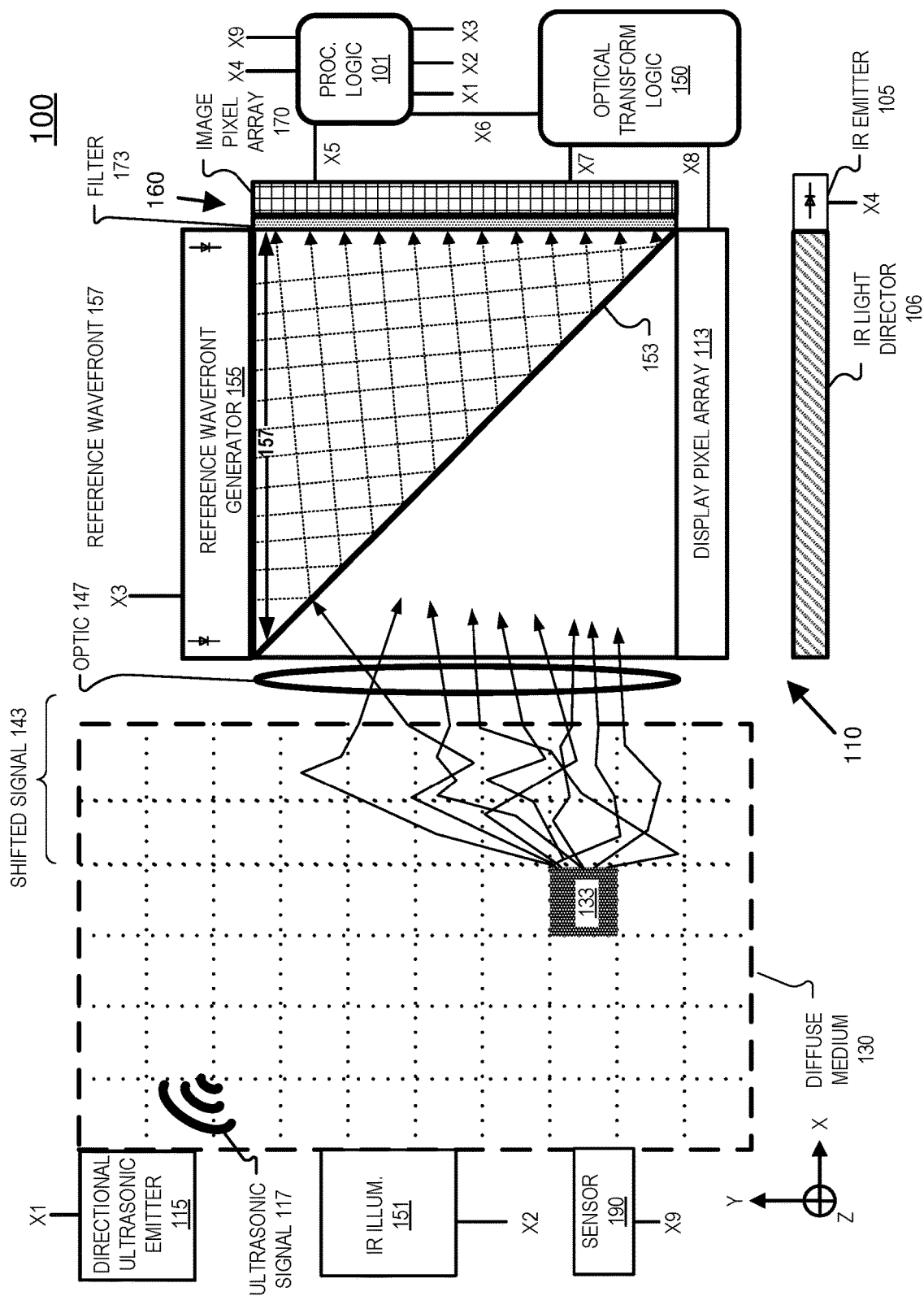
Figure 1C:
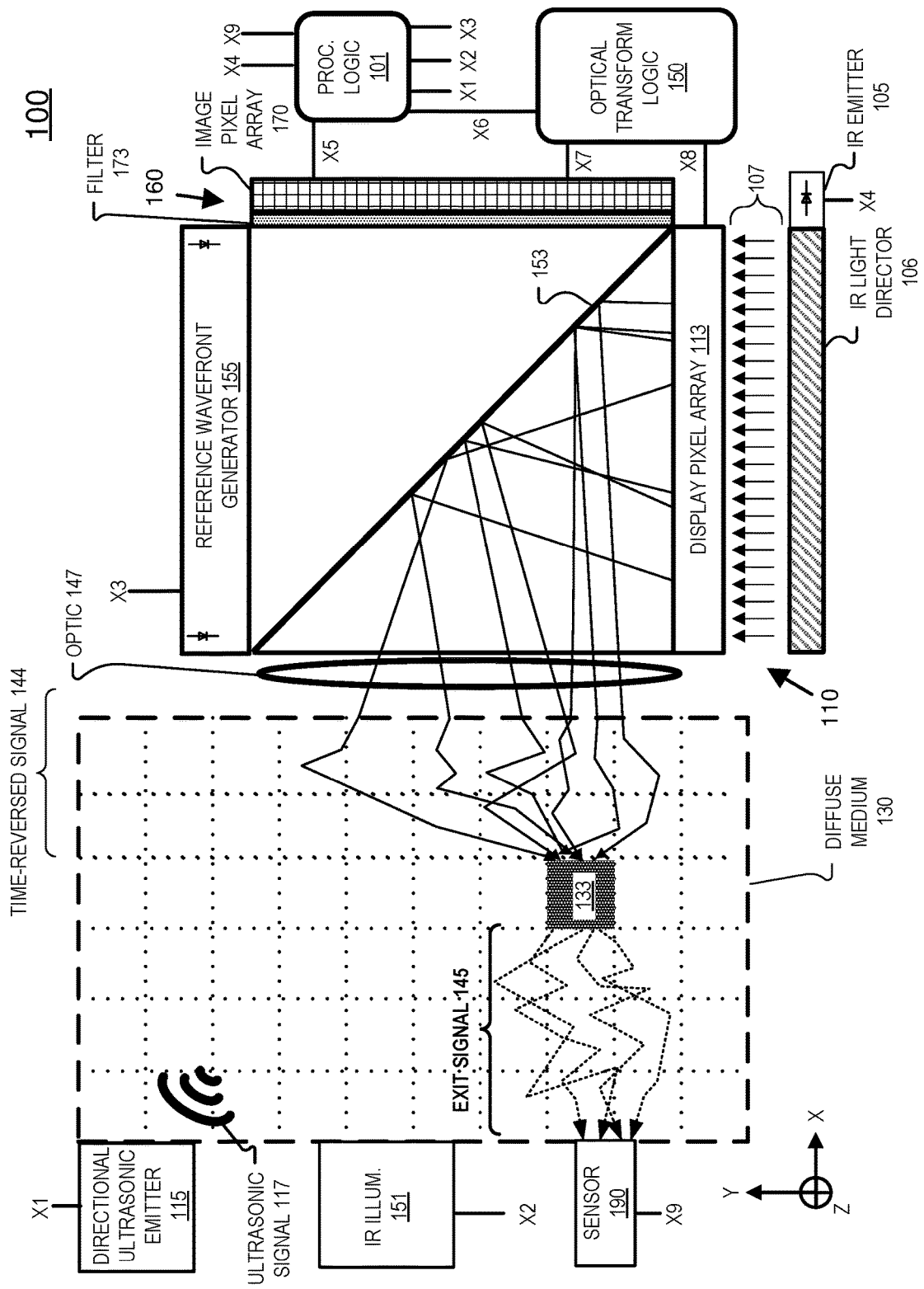

FIGS. 1A-1C illustrate an example imaging system that includes a display pixel array, an image pixel array, and a beam splitter, in accordance with an embodiment of the disclosure. In FIG. 1A, imaging system 100 includes processing logic 101, a spatial light modulator (SLM) 110, and image module 160. Imaging module 160 includes image pixel array 170 and filter(s) 173. In FIG. 1A, imaging system 100 also includes a directional ultrasonic emitter 115 coupled to be driven by processing logic 101. In FIG. 1A, SLM 110 includes an infrared emitter 105, an infrared light director 106, and a display pixel array 113. Display pixel array 113 may be an LCD (liquid crystal display), for example. The LCD display may be an active-matrix (using thin-film-transistors) or a passive matrix LCD. In one embodiment, the LCD display has pixels that are smaller than 7 microns. In other embodiments, SLM 110 may include a reflective architecture such as a liquid-crystal-on silicon (LCOS) display being illuminated by infrared light, for example. Other known transmissive and reflective display technologies may also be utilized as SLM 110. System 100 may include a plurality of discrete devices that incorporate components of system 100, in some embodiments.

Processing logic 101 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 101 to store instructions to execute operations and/or store data. A "memory" or "memories" described in this disclosure may include volatile or non-volatile memory architectures.

System 100 includes an infrared illuminator 151. Processing logic 101 is coupled to selectively activate IR illuminator 151 via output X2, in the illustrated embodiment. Infrared illuminator 151 may include an infrared laser generating a general illumination emission 152. Of course, an infrared laser may generate monochromatic coherent infrared light. Monochromatic light may be defined as light within a 4 nm frequency band, for example. The infrared light that IR illuminator 151 emits may be centered around a frequency in the 680-1000 nm range. In one embodiment, the infrared light that IR illuminator 151 emits may be centered around a frequency in the 1600-1700 nm range. In one example, IR illuminator 151 generates monochromatic light centered around 680 nm. In one example, IR illuminator 151 generates monochromatic light centered around 850 nm. The infrared illuminator 151 is disposed to direct the general illumination emission 152 into the diffuse medium 130. In the context of tissue, general illumination emission 152 will be significantly scattered within tissue within as little as 1 cm of depth into the tissue when tissue is the diffuse medium 130. At least a portion of the general illumination emission 152 will encounter voxel 133, as illustrated in FIG. 1A.

System 100 also includes an ultrasonic emitter 115. Ultrasonic emitter 115 is configured to focus an ultrasonic signal 117 to a point in three-dimensional space. In the medical context, the ultrasonic emitter 115 is configured to focus an ultrasonic signal 117 to a voxel within the human body. The voxel may be within the brain, abdomen, or uterus, for example. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of illumination emission 152 that encounters the voxel by wavelength-shifting that portion of illumination emission 152 that propagates through that voxel.

In FIG. 1B, the wavelength-shifted portion of the general illumination emission 152 is illustrated as shifted infrared imaging signal 143. Being influenced by ultrasonic signal 117, shifted signal 143 has a different wavelength (hereinafter referred to as lambda-two) than general illumination emission 152 (referred to as lambda-one). In some embodiments, the delta between lambda-one and lambda-two may be less than 1 nanometer. In an embodiment, the delta between lambda-one and lambda-two may be less than 20 femtometer.

System 100 receives (at least a portion of) shifted infrared imaging signal 143. An input optic 147 may optionally be included in system 100. Input optic 147 may receive shifted signal 143 and direct the shifted signal 143 to be incident on image pixel array 170. In one embodiment, input optic 147 is configured to filter out an angled portion of the shifted signal 143. In one embodiment, the angled portion of the shifted signal 143 has a plus-or-minus angle of incidence upon the input optic 147 that is higher than an angle threshold. In one embodiment, the sine of twice the angle threshold is approximately equivalent to a wavelength of the shifted signal 143 (lambda-two) divided by twice a distance between two pixels of the image pixel array 170. In one embodiment, the angle threshold is between five and seven degrees.

Still referring to FIG. 1B, reference wavefront generator 155 generates an infrared reference wavefront 157 having the lambda-two wavelength so that infrared reference wavefront 157 interferes with the incoming shifted signal 143. Reference wavefront generator 155 may include one or more laser diodes and corresponding optics to generate a substantially uniform wavefront. Processing logic 101 is coupled to selectively activate reference wavefront generator 155 via output X3, in the illustrated embodiment.

A first portion of the infrared reference wavefront 157 is redirected to the image pixel array 170 by beam splitter 153 while a second remaining portion of wavefront 157 passes through beam splitter 153. Shifted signal 143 encounters beam splitter 153 and a first portion of the shifted signal 143 passes through beam splitter 153 while the remaining second portion of the shifted signal 143 is reflected by beam splitter 153. The first portion of the shifted signal 143 that passes through beam splitter 153 interferes with the first portion of wavefront 157 that is redirected to image pixel array 170 and image pixel array 170 captures an infrared image of the interference between shifted signal 143 and infrared reference wavefront 157.

In one embodiment, reference wavefront generator 155 is disposed to deliver the infrared reference wavefront 157 to the image pixel array 170 at an angle to a pixel plane of the image pixel array 170. Image pixel array 170 may include image pixels disposed in a two-dimensional rows and columns that define the pixel plane of the image pixel array 170. In one embodiment, the angle is between five and seven degrees so that the infrared reference wavefront 157 encounters the image pixels of image pixel array 170 at a non-orthogonal angle. Angling the infrared reference wavefront 157 may change the interference orientation and size between shifted signal 143 and wavefront 157, which may enable better signal isolation at the image pixel array 170. Processing logic 101 is coupled to initiate the image capture by image pixel array 170 via output X5, in the illustrated embodiment.

A linear polarizer may be included in system 100 to polarize shifted signal 143 to have the same polarization orientation as infrared reference wavefront 157. The light source of reference wavefront generator 155 may generate linear polarized light which imparts a polarization orientation to infrared reference wavefront 157. The linear polarizer may be included in optic 147, filter 173, or in a linear polarizer disposed between optic 147 and filter 173.

In the illustrated embodiment, an infrared filter 173 is disposed between beam splitter 153 and image pixel array 170. Infrared filter 173 may pass the wavelength of infrared light emitted by reference wavefront generator 155 (lamda-two) and reject ambient light in a bandpass that is 10 nm or greater.

Image pixel array 170 may be implemented with an a-Si (amorphous Silicon) thin film transistors, in some embodiments or a CMOS (Complementary Metal-Oxide-Semiconductor) image sensor, in some embodiments. Image pixel array 170 can be a commercially available image sensor. In one embodiment, image pixel array 170 has image pixels having a pixel pitch of 3.45 microns. In one embodiment, image pixel array 170 has image pixels having a pixel pitch of 1.67 microns. The pixel resolution of image pixel array 170 may vary depending on the application. In one embodiment, the image pixel array 170 is 1920 pixels by 1080 pixels. In one embodiment, the image pixel array is 40 Megapixels or more. Image pixel array 170 can capture an infrared image of an interference between shifted signal 143 and IR reference wavefront 157 by measuring the image charge generated in each pixel during a given integration period that is determined by an electronic shutter. The electronic shutter may be a global shutter (where each pixel measures the incident light during a same time period) or a rolling shutter. The electronic shutter can be actuated by processing logic 101 via input/output X5. Input/output X5 may include digital input/output lines as well as a data bus. Image pixel array 170 is communicatively coupled to optical transform logic 150 to send the captured infrared image(s) to optical transform logic 150 for further processing. In some embodiments, the integration period of the pixels of the image pixel array 170 is determined by the length of a laser pulse. Image pixel array 170 may include a local (on-board) digital signal processor (DSP), in some embodiments, and optical transform logic 150 may receive the captured infrared images from the DSP.

Optical transform logic 150 is coupled to image pixel array 170 via communication channel X7, in the illustrated embodiment. Optical transform logic is also communicatively coupled to processing logic 101 via communication channel X6. Optical transform logic 150 is coupled to receive the captured infrared image from the image pixel array and provide a holographic pattern to be driven onto the display pixel array 113. The optical transform logic 150 is configured to extract phase data of the interference captured by the infrared image and the holographic pattern is generated from the phase data. A more detailed description of example optical transform logic is described in U.S. patent application Ser. No. 15/942,480, which is hereby incorporated by reference.

Referring now to FIG. 1C, display pixel array 113 is configured to generate an infrared holographic imaging signal 144 (reconstruction of signal 143) according to a holographic pattern driven onto the array 113. Optical transform logic 150 is coupled to provide the array 113 the holographic pattern via communication channel X8.

In FIG. 1C, display pixel array 113 is illustrated as a transmissive LCD that is illuminated by infrared wavefront 107. In the illustrated embodiment, infrared (IR) emitter 105 is coupled to be driven by output X4 of processing logic 101. When processing logic 101 turns on (activates) IR emitter 105, infrared light propagates into IR light director 106. IR light director 106 may be a light guide plate similar to those found in conventional edge lit LCDs. IR light director 106 may be a slim prism utilizing TIR (total internal reflection). IR light director 106 redirects the infrared light toward display pixel array 113. IR light director 106 may include a sawtooth grating to redirect the infrared light toward array 113. IR emitter 105 is an infrared laser diode that emits monochromatic infrared light, in one embodiment.

Steerable infrared beams can be generated by SLM 110 by driving different holographic patterns onto display pixel array 113. Each different holographic pattern can steer (focus) the infrared light in a different direction. The directional nature of the infrared beam is influenced by the constructive and destructive interference of the infrared light emitted from the pixels of SLM 110. As an example, a holographic pattern that includes different "slits" at different locations can generate different infrared beams. The "slits" can be generated by driving all the pixels in the display pixel array 113 to "black" (not transmissive) except for the pixels where the "slits" are located are driven to be "white" (transmissive) to let the infrared light propagate through. The pixel size of display pixel array 113 may be 1 micron, although in some embodiments pixels sized up to 10 times the wavelength of the infrared light can be used. In one example, if IR emitter 105 is an 850 nm laser diode, the pixel size of SLM 110 may be 850 nm. The pixel size influences the angular spread of a hologram since the angular spread is given by the Grating Equation:

$$\sin(\theta) = m\lambda/d \qquad \text{(Equation 1)}$$

where θ is the angular spread of light, m is an integer number and the order of diffraction, and d is the distance of two pixels (a period). Hence, smaller pixel size generally yields more design freedom for generating holographic beams, although pixels sizes that are greater than the wavelength of light can also be used to generate holographic imaging signals. Display pixel array 113 may include square pixels (rather than the rectangular pixels in conventional RGB LCDs) so that the Grating Equation is applicable in both the row dimension and column dimension of the display pixel array 113.

In the illustrated embodiment, processing logic 101 selectively activates infrared emitter 105 and infrared light director 106 directs the infrared light to illuminate display pixel array 113 as infrared wavefront 107 while the holographic pattern is driven onto array 113. Infrared wavefront 107 is the same wavelength as infrared reference wavefront 157. Processing logic 101 may deactivate reference wavefront generator 155 while display pixel array 113 is being illuminated by infrared wavefront 107. Processing logic 101 may be configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Display pixel array 113 generates an infrared holographic imaging signal when the holographic pattern is illuminated by infrared wavefront 107 and the infrared holographic imaging signal is redirected by beam splitter 153 to exit system 100 as a reconstruction 144 (in reverse) of the shifted signal 143 that entered system 100. Reconstructed signal 144 follows (in reverse) whatever scattered path that shifted signal 143 took from voxel 133 to beam splitter 153 so reconstructed signal 144 is essentially "focused" back onto voxel 133.

Voxel 133 may absorb or scatter reconstructed signal 144 according to biological and/or optical characteristics of voxel 133 and sensors may measure an exit signal 145 of the reconstructed signal 144 that encounters voxel 133. System 100 may optionally include a sensor 190 coupled to processing logic 101 via an input/output X9 to initiate light measurement of exit signal 145 and pass the light measurement to processing logic 101. Although exit signal 145 is illustrated as being directed to sensor 190, the illustrated exit signal 145 is only a portion of the exit signal 145 that will be generated from signal 144 encountering voxel 133 and exit signal 145 will have many exit points from diffuse medium in addition to the illustrated portion of exit signal 145. The sensors that measure this exit signal may simply measure the amplitude of the exit signal. Sensor 190 may be a photodiode or a CMOS image sensor, for example. In one embodiment, the image pixel array 170 is used to measure the amplitude and/or phase of exit signal 145. The amplitude and/or phase of the exit signal 145 may be used to generate an image of diffuse medium 130. A reconstructed signal 144 may be directed to voxel 133 multiple times (with multiple corresponding measurements of exit signal 145) so that biological changes in voxel 133 may be recorded over a time range.

System 100 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array gives display pixel array 113 the ability to generate steerable holographic infrared beams that can focus an infrared signal (e.g. 144) to different voxels in three-dimensional space to facilitate the raster scanning of diffuse medium 130.

In one embodiment, processing logic 101 is configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Figure 2A:
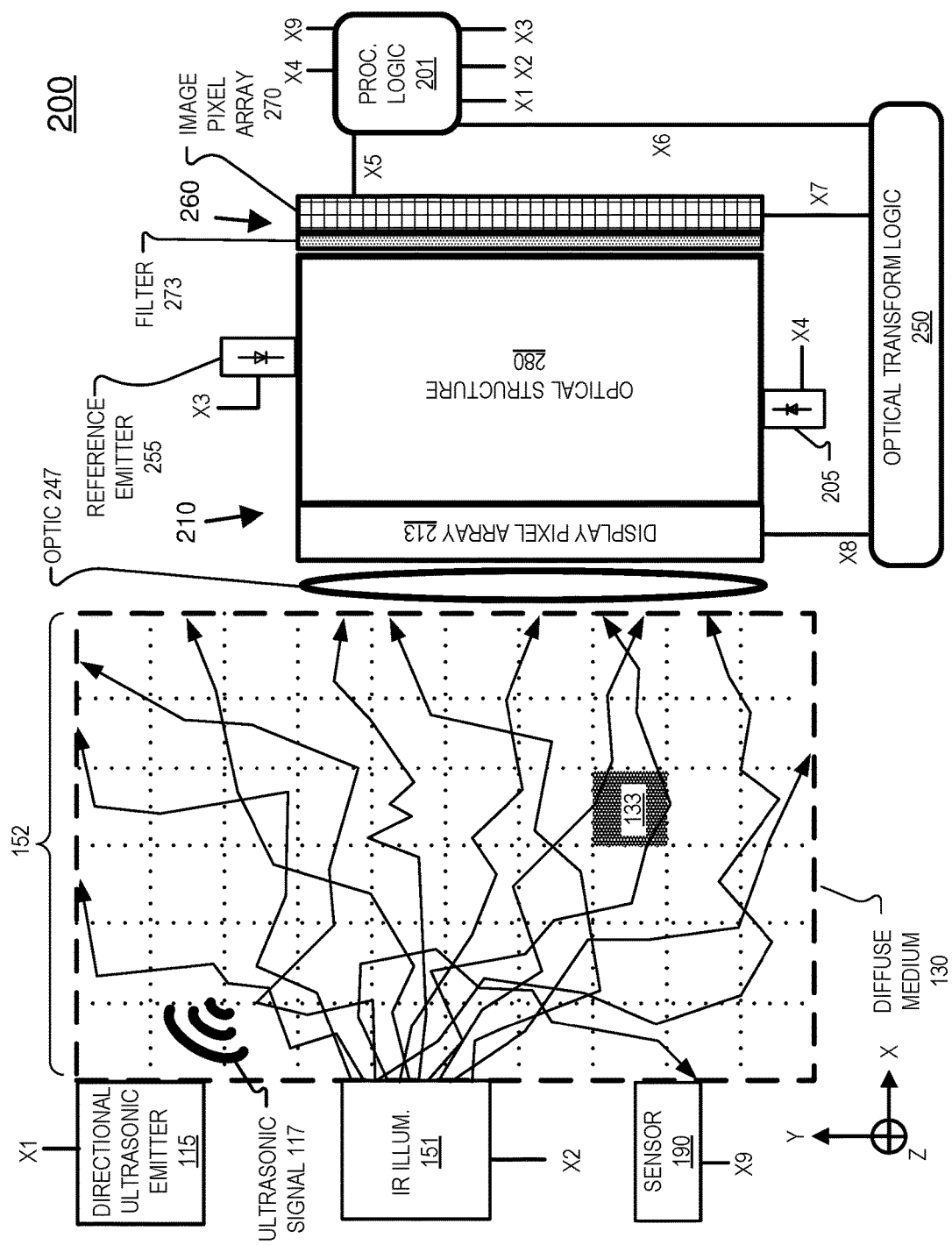
FIGS. 2A-2C illustrate an example imaging system that includes an image pixel array receiving an exit signal through a display pixel array, in accordance with an embodiment of the disclosure.
Figure 2B:
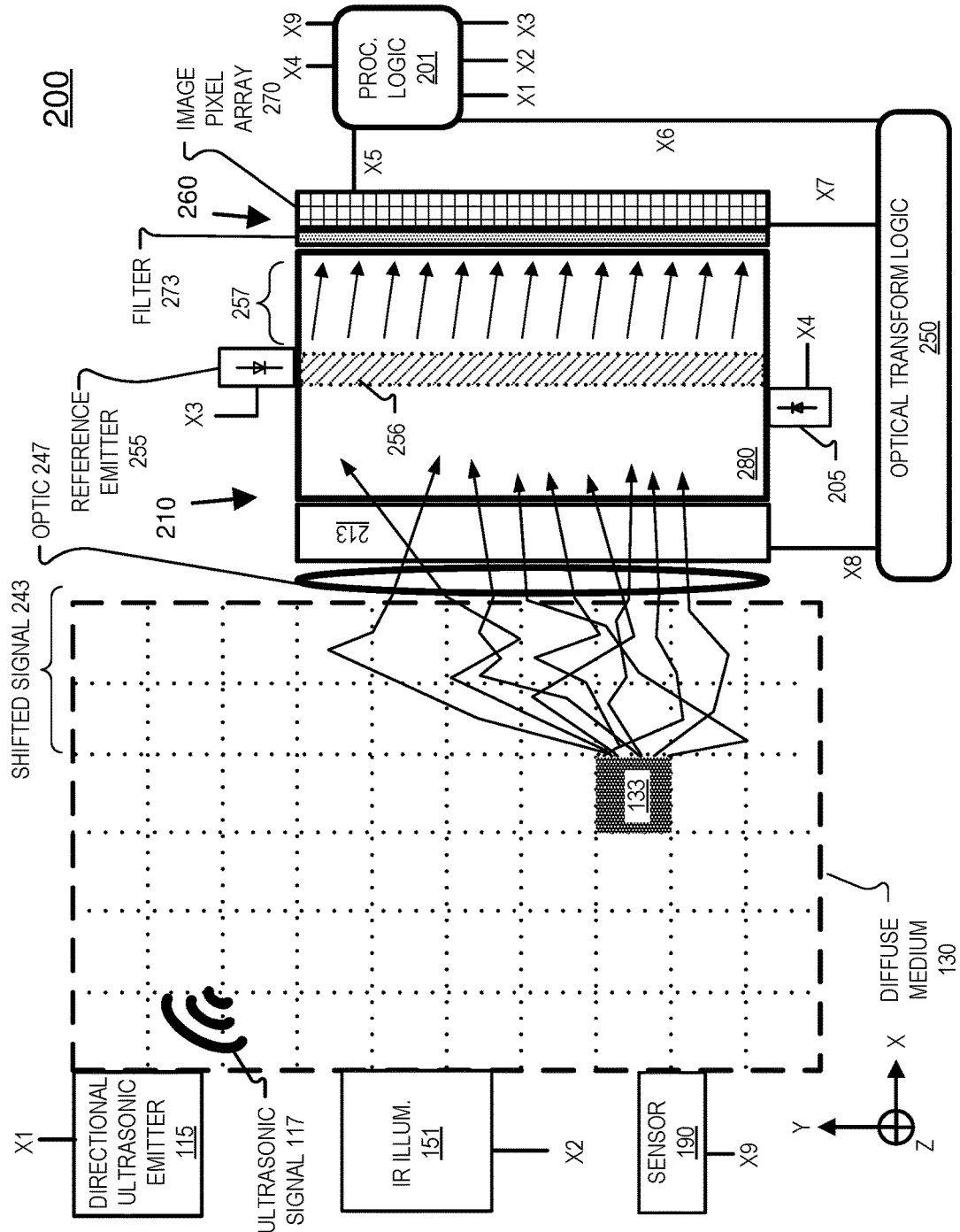
Figure 2C:
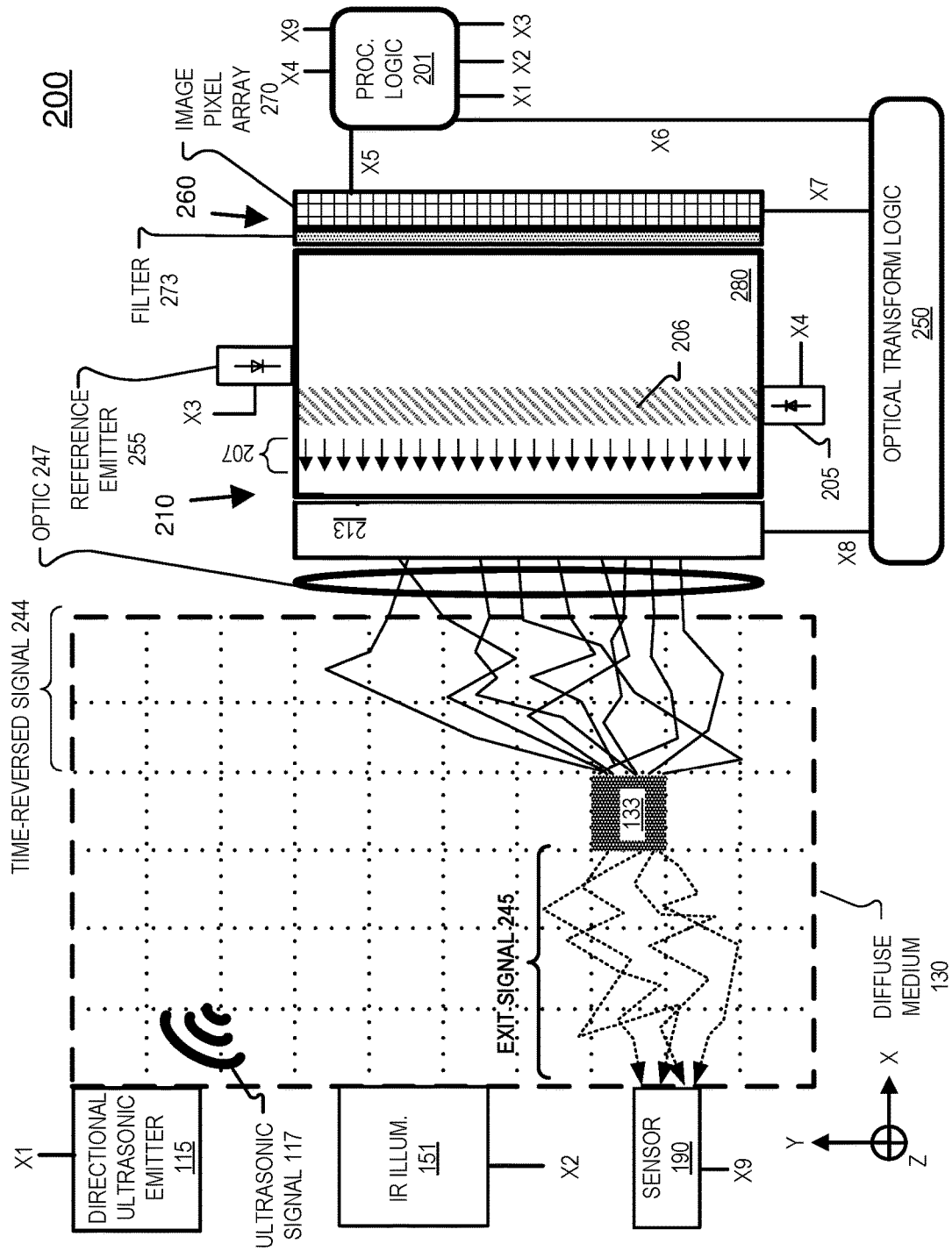

FIGS. 2A-2C illustrate an example imaging system 200 that includes an optical structure disposed between a display pixel array and an image pixel array, in accordance with an embodiment of the disclosure. System 200 illustrated in FIGS. 2A-2C functions similarly to system 100 of FIGS. 1A-1C although there are differences associated with the different positioning of the SLM 210, the imaging module 260, and the addition of optical structure 280.

Similarly to FIG. 1A, in FIG. 2A, processing logic 201 is coupled to drive directional ultrasonic emitter 115 to focus ultrasonic signal 117 to different locations in three-dimensional space, via output X1. Processing logic 201 is also coupled to selectively activate IR illuminator 151 via output X2, in the illustrated embodiment. System 200 may include a plurality of discrete devices that incorporate components of system 200, in some embodiments.

Imaging module 260 includes image pixel array 270 and filter(s) 273. In FIG. 2A, imaging system 200 also includes a directional ultrasonic emitter 115 coupled to be driven by processing logic 201. SLM 210 includes an infrared emitter 205, an infrared light director 206 (illustrated in FIG. 2C), and a display pixel array 213. Display pixel array 213 is a transmissive pixel array, in FIG. 2A.

Processing logic 201 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 201 to store instructions to execute operations and/or store data. A "memory" or "memories" described in this disclosure may include volatile or non-volatile memory architectures.

With ultrasonic signal 117 focused on voxel 133 in diffuse medium 130, IR illuminator 151 is selectively activated to emit general illumination emission 152 and a portion of emission 152 encounters voxel 133.

In FIG. 2B, the wavelength-shifted portion of the general illumination emission 152 is illustrated as shifted infrared imaging signal 243. Being influenced by ultrasonic signal 117, shifted infrared imaging signal 243 has a different wavelength (lambda-two) than general illumination emission 152 (lambda-one).

System 200 receives (at least a portion of) shifted signal 243. An input optic 247 may optionally be included in system 200. Input optic 247 may receive shifted signal 243 and focus the shifted signal 243 to be incident on image pixel array 270. In one embodiment, input optic 247 is configured to filter out an angled portion of the shifted signal 243, as described with regard to an embodiment of input optic 147.

Still referring to FIG. 2B, reference emitter 255 is configured to selectively emit an infrared reference light having the lambda-two wavelength so that infrared reference wavefront 257 interferes with the incoming shifted signal 243. Reference emitter 255 may include one or more laser diodes and reference director optic 256 in optical structure 280 may direct the lambda-two infrared reference light to image pixel array 270 as a substantially uniform infrared reference wavefront 257. Processing logic 201 is coupled to selectively activate reference emitter 255 via output X3, in the illustrated embodiment.

A linear polarizer may be included in system 200 to polarize shifted signal 243 to have the same polarization orientation as infrared reference wavefront 257. Reference emitter 255 may generate linear polarized light which imparts a polarization orientation to infrared reference wavefront 257. The linear polarizer may be included in optic 247, filter 273, or optical structure 280.

Shifted signal 243 may encounter input optic 247, display pixel array 213, and optical structure 280 prior to becoming incident upon image pixel array 270. The shifted signal 243 interferes with infrared reference wavefront 257 and image pixel array 270 captures an infrared image of the interference between shifted signal 243 and infrared reference wavefront 257. To allow shifted signal 243 to pass through display pixel array 213, each of the display pixels of the display pixel array 213 may be driven to a transmissive state while IR illuminator 151 and reference emitter 255 are activated.

In one embodiment, reference director optic 256 is configured to deliver the infrared reference wavefront 257 to the image pixel array 270 at an angle to a pixel plane of the image pixel array 270. Processing logic 201 is coupled to initiate the image capture by image pixel array 270 via output X5, in the illustrated embodiment.

In the illustrated embodiment, an infrared filter 273 is disposed between optical structure 280 and image pixel array 270. Infrared filter 273 may include the same configuration as infrared filter 173. Image pixel array 270 may include the same configuration as image pixel array 170. Image pixel array 270 is communicatively coupled to optical transform logic 250 to send the captured infrared image(s) to optical transform logic 250 for further processing. Optical transform logic 250 is coupled to image pixel array 270 via communication channel X7, in the illustrated embodiment. Optical transform logic 250 is coupled to receive the captured infrared image from the image pixel array 270 and provide a holographic pattern to be driven onto the display pixel array 213. The optical transform logic 250 is configured to extract phase data of the interference captured by the infrared image and the holographic pattern is generated from the phase data.

Referring now to FIG. 2C, display pixel array 213 is configured to generate an infrared holographic imaging signal 244 according to a holographic pattern driven onto the array 213. Optical transform logic 250 is coupled to provide the array 213 the holographic pattern to array 213 via communication channel X8.

In FIG. 2C, display pixel array 213 is illustrated as a transmissive LCD that is illuminated by infrared wavefront 207. In the illustrated embodiment, infrared emitter 205 is coupled to be driven by output X4 of processing logic 201. When processing logic 201 turns on (activates) IR emitter 205, infrared light propagates into IR light director 206. IR light director 206 redirects the infrared light toward display pixel array 213. IR emitter 205 is an infrared laser diode that emits monochromatic infrared light, in one embodiment.

In the illustrated embodiment, processing logic 201 selectively activates infrared emitter 205 and infrared light director 206 directs the infrared light to illuminate display pixel array 213 as infrared wavefront 207 while the holographic pattern is driven onto array 213. Infrared wavefront 207 is the same wavelength as infrared reference wavefront 257. Processing logic 201 may deactivate reference emitter 255 while display pixel array 213 is being illuminated by infrared wavefront 207. Processing logic 201 may be configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

Display pixel array 213 generates an infrared holographic imaging signal 244 when the holographic pattern is illuminated by infrared wavefront 207 and the infrared holographic imaging signal 244 exits system 200 as a reconstruction (in reverse) of the shifted signal 243 that entered system 200. Reconstructed signal 244 follows (in reverse) whatever scattered path that shifted signal 243 took from voxel 133 to the display pixel array 213 so reconstructed signal 244 is essentially "focused" back onto voxel 133.

Voxel 133 may absorb or scatter reconstructed signal 244 according to biological characteristics of voxel 133 and sensors may measure an exit signal 245 of the reconstructed signal 244 that encounters voxel 133. System 200 may optionally include a sensor 190 coupled to processing logic 201 via an input/output X9 to initiate light measurement of exit signal 245 and pass the light measurement to processing logic 201. Although exit signal 245 is illustrated as being directed to sensor 190, the illustrated exit signal 245 is only a portion of the exit signal 245 that will be generated from signal 244 encountering voxel 133 and exit signal 245 will have many exit points from diffuse medium in addition to the illustrated portion of exit signal 245. The sensors that measure this exit signal may simply measure the amplitude of the exit signal. In one embodiment, the image pixel array 270 is used to measure the amplitude and/or phase of exit signal 245. The amplitude and/or phase of the exit signal 245 may be used to generate an image of diffuse medium 130. A reconstructed signal 244 may be directed to voxel 133 multiple times (with multiple corresponding measurements of exit signal 245) so that biological changes in voxel 133 may be recorded over a time range.

System 200 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array 213 gives display pixel array 213 the ability to generate steerable holographic infrared beams that can focus the reconstructed signal (e.g. 244) to different voxels in three-dimensional space to facilitate the raster scanning of diffuse medium 130.

In one embodiment, processing logic 201 is configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

In system 200, image pixel array 270 is disposed in a parallel plane to display pixel array 213. However, in some embodiments, image pixel array 270 may be angled to increase the signal of interference between the infrared reference wavefront 257 and shifted signal 243. In system 100, image pixel array 170 is illustrated as being in a plane that is orthogonal to display pixel array 113. However, in some embodiment, image pixel array 170 may be angled to increase the signal of interference between the infrared reference wavefront 157 and shifted signal 143.

Although not specifically illustrated in FIGS. 1A-2C, infrared illuminator 151, reference wavefront generator 155 and infrared emitter 105 may be fiber optic outputs that are provided light via fiber optic from a single laser source. Similarly, infrared illuminator 151, reference emitter 255, and infrared emitter 205 may be provided light via fiber optic from a single laser source. The light from the single laser source may be modulated (e.g. by an acoustic optical modulator) to direct the laser light to the proper fiber optic for illumination. A micro-electro-mechanical system (MEMS) mirror, a digital micromirror device (DMD), or a mirror galvanometer may be used to selectively couple light from a single source into different fiber optic paths, in different embodiments. The light from the single laser source may also be selectively wavelength-shifted (e.g. by an acoustic optical modulator) to provide IR illuminator 151 with lambda-one wavelength light and to provide reference elements 105, 205, 155, and 255 with lambda-two wavelength light.

Figure 3:
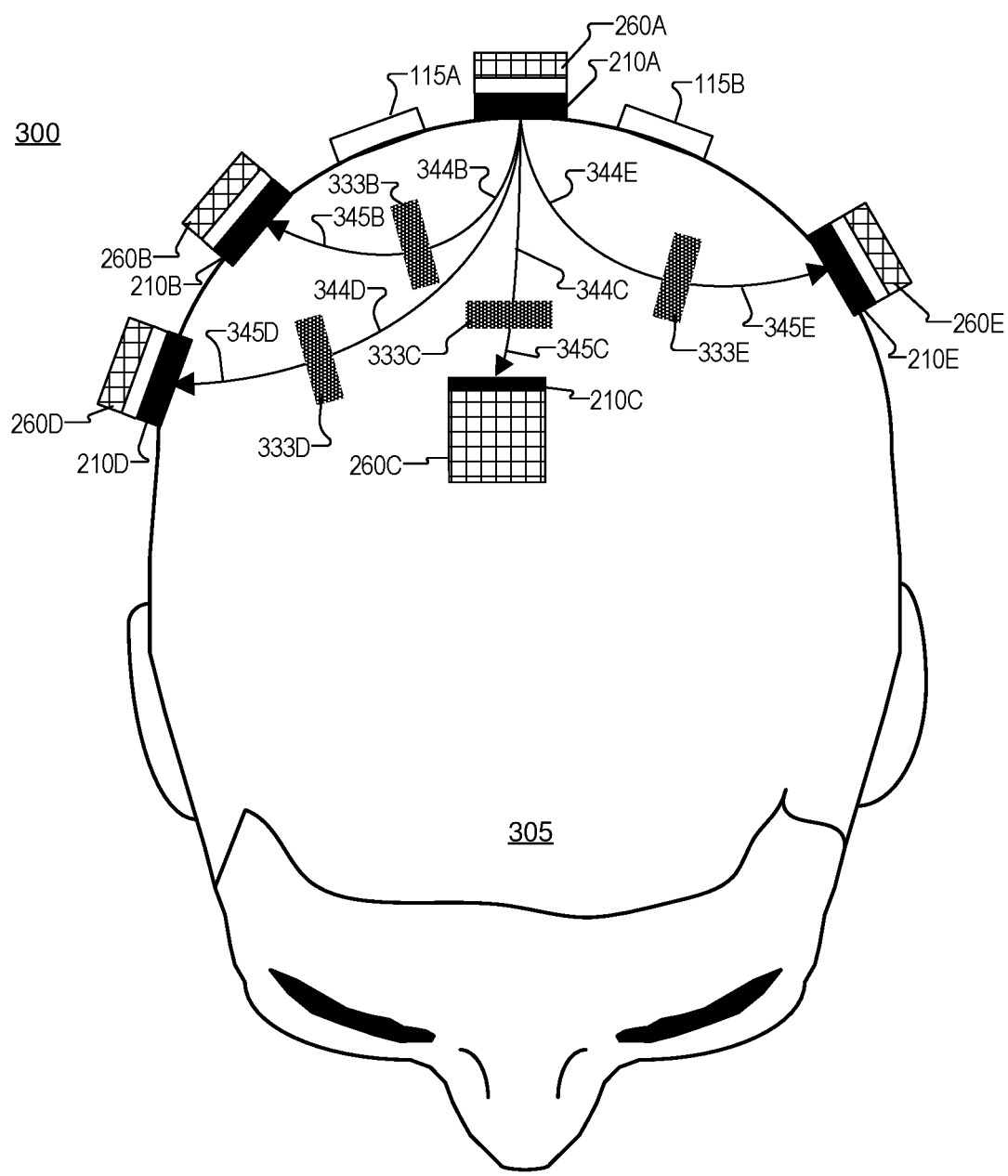
FIG. 3 illustrates an example placement of components of an imaging system in relationship to a human head, in accordance with an embodiment of the disclosure.

FIG. 3 illustrates an example placement of components of an imaging system 300 in relationship to a human head, in accordance with an embodiment of the disclosure. FIG. 3 is a top-down view of a human head 305. Imaging system 300 includes SLMs 210A-210E and imaging modules 260A-260E arranged as in system 200, and directional ultrasonic emitters 115A and 115B. Of course, SLMs 110 and imaging modules 160 may also be used instead of SLMs 210 and imaging modules 260 in imaging system 300. FIG. 3 shows that SLM 210A may generate multiple reconstructed infrared signals 344 that are directed to image different voxels 333 of the brain while the exit signals 345 are imaged by different imaging modules 260. The other SLMs 210B-210E may also generate reconstructed infrared signals 344 (not illustrated) directed to voxels where the exit signals are imaged by each of imaging modules 260A-E. Scientific literature suggests that the penetration depth of infrared light into tissue is around 10 cm so multiple SLMs 210 and imaging modules 160 may be needed to image the entire brain or other tissue. Although not illustrated, sensors 190 may also be placed around a diffuse medium such as human head 305 to measure the exit signals 345. A wearable hat may include system 300 so that system 300 can be worn as a wearable, in some embodiments. Other wearables may also include all or part of system 300.

Figure 4A:
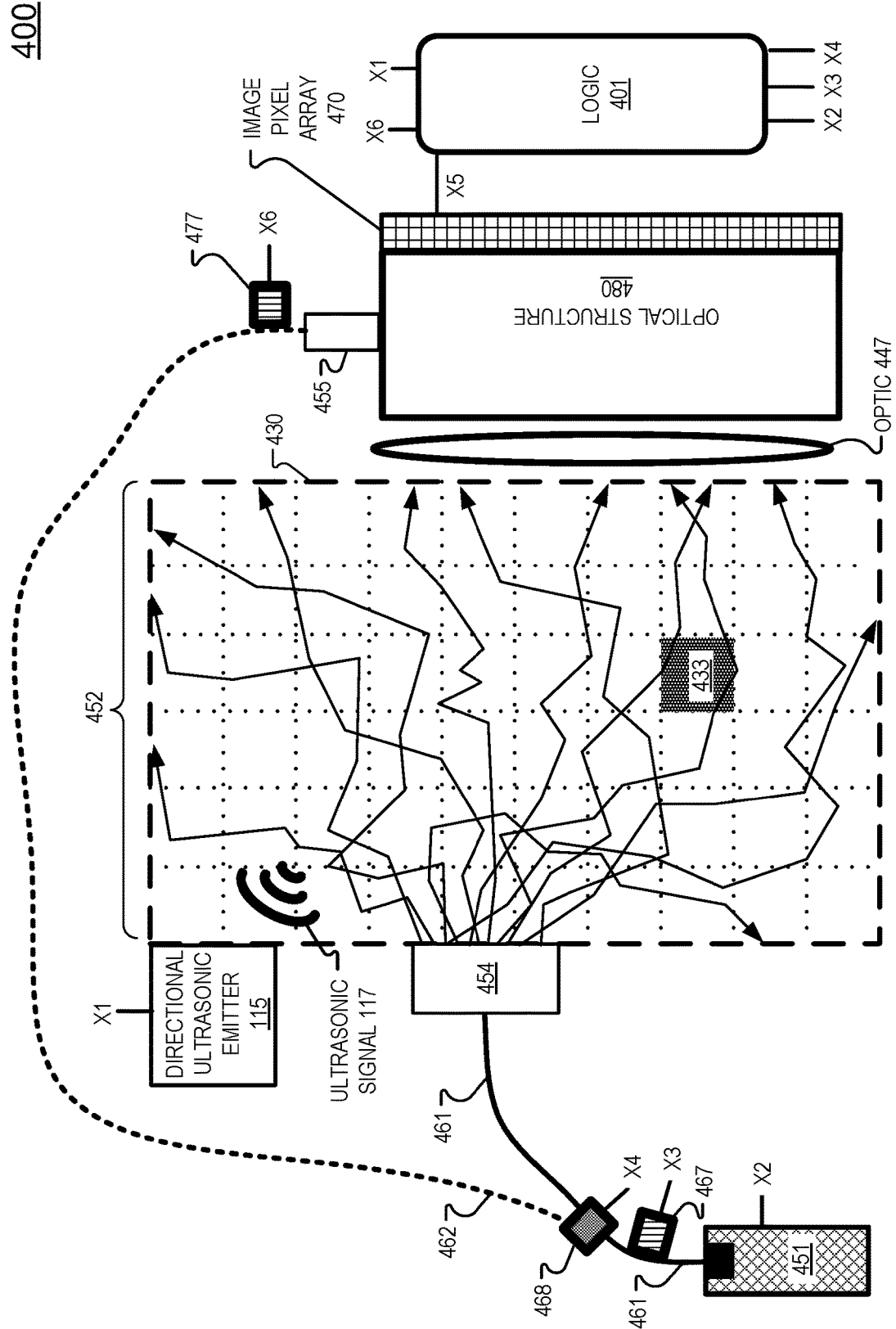
FIGS. 4A-4B illustrate an example imaging system that includes an image pixel array and an energy meter optically coupled to measure energy level data of a light pulse emitted by a light source, in accordance with an embodiment of the disclosure.
Figure 4B:
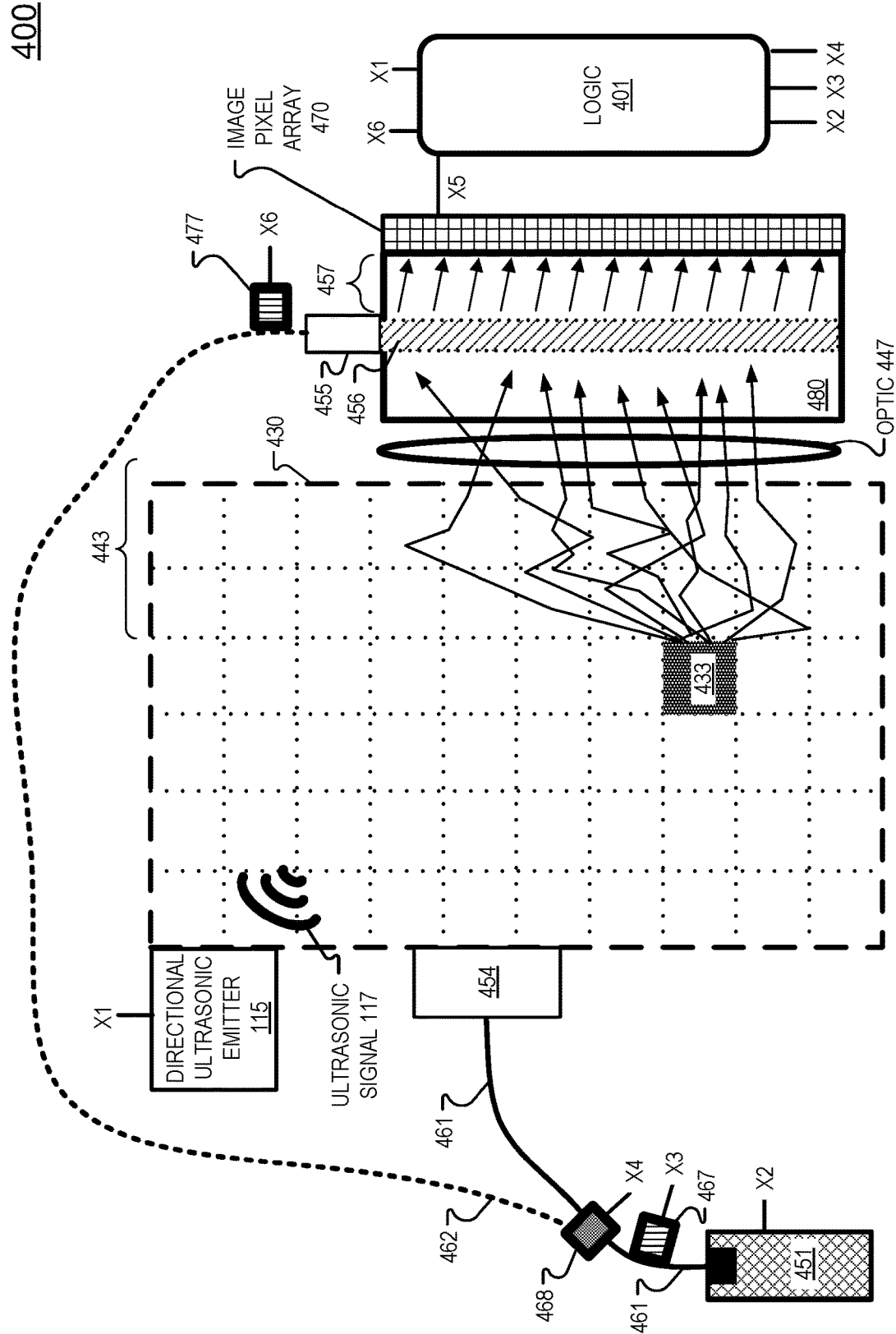

FIGS. 4A-4B illustrate an example imaging system that includes an image pixel array and an energy meter optically coupled to measure energy level data of a light pulse emitted by a light source, in accordance with an embodiment of the disclosure. System 400 illustrated in FIGS. 4A-4B does not include a display pixel array, as in FIGS. 1A-2C. System 400 may include a plurality of discrete devices that incorporate components of system 400, in some embodiments.

In FIG. 4A, processing logic 401 is coupled to drive directional ultrasonic emitter 115 to focus ultrasonic signal 117 to different locations in three-dimensional space, via communication channel X1. Processing logic 401 is also coupled to control emission of light pulses from light source 451 via communication channel X2.

Processing logic 401 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 401 to store instructions to execute operations and/or store data. A "memory" or "memories" described in this disclosure may include volatile or non-volatile memory architectures.

Light source 451 may be a pulsed infrared laser configured to emit pulsed infrared light, in some embodiments. A pulsed infrared laser may emit an infrared pulse having a pulse width of approximately 100-250 nanoseconds, at a frequency of 360 Hz. or greater, and having an energy of approximately 15-150 mJ per pulse. The narrow-band infrared wavelength of the infrared pulse may be 725 nm, 825 nm, 1064 nm, or 1450 nm, for example.

Figure 7:
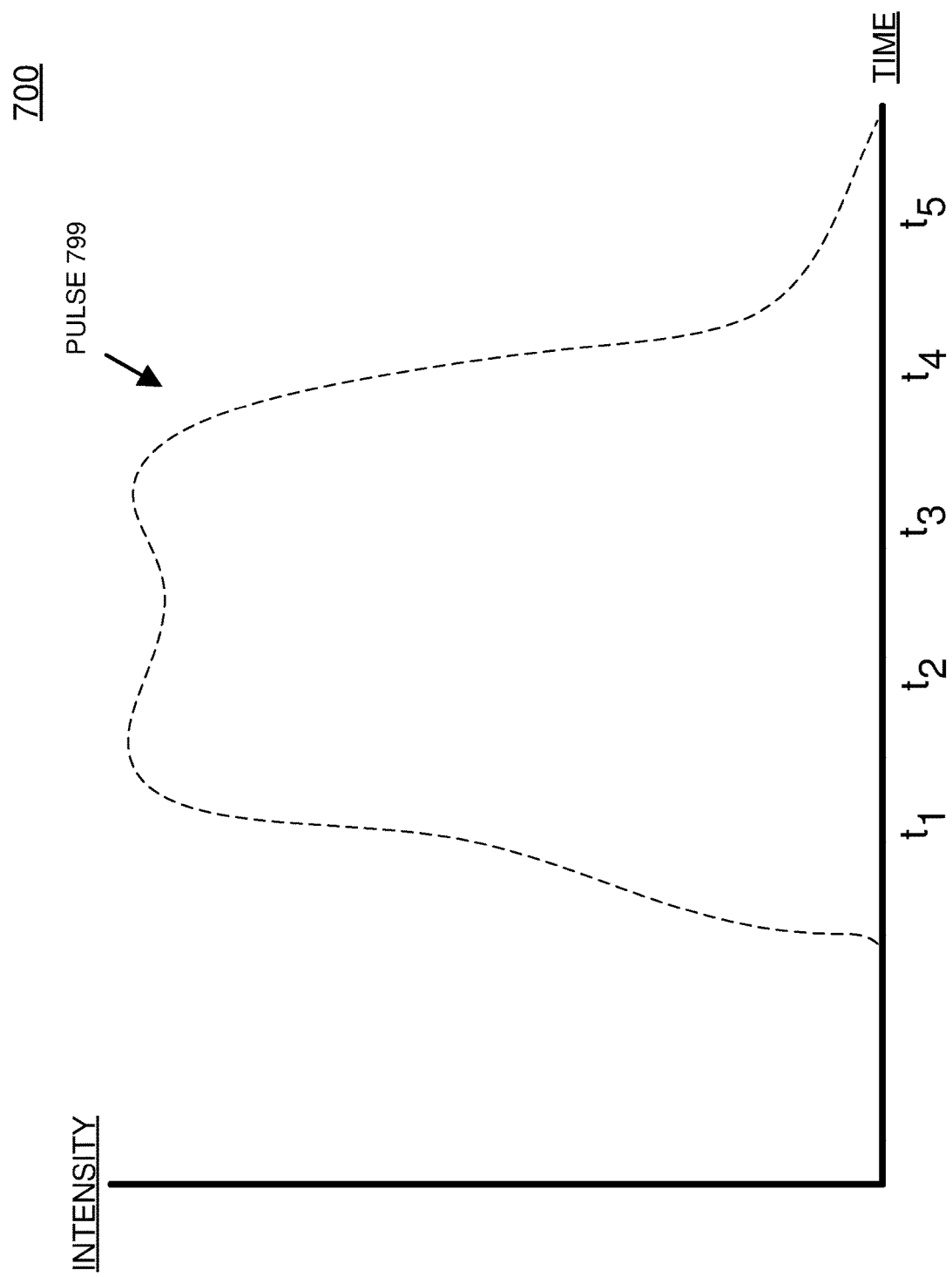
FIG. 7 illustrates a chart including an example light pulse having different intensity measurements at different measurement times, in accordance with an embodiment of the disclosure.

The light pulses from light source 451 are emitted into optical fiber 461, in FIG. 4A. Energy meter 467 is optically coupled to measure an energy level of a given light pulse. Processing logic 401 synchronize the measurement and emission of a light pulse via communication channels X2 and X3. In FIG. 4A, energy meter 467 is optically coupled to measure an energy level of the light pulse propagating in optical fiber 461. Energy meter 467 generates energy level data of the measured energy level of the light pulse and provides the energy level data to logic 401 via communication channel X3, in the illustrated embodiment. In one embodiment, energy meter 467 includes a photodiode. The photodiode may take a plurality of light intensity measurements over time to provide a temporal profile of the emitted light pulse. FIG. 7 illustrates a chart 700 including an example light pulse 799 having different intensity measurements at different measurement times t1, t2, t3, t4, and t5, for example. The temporal profile may be included in the energy level data. In one embodiment, energy meter 467 includes a beam camera that captures an image of the emitted light pulse to provide the spatial beam shape of the light pulse. The spatial beam shape determined by a beam camera may be included in the energy level data.

FIG. 4A includes a pulse modulator 468 that may optionally be included in some example systems. Pulse modulator 468 may be an acoustic optical modulator (AOM), for example. Pulse modulator 468 may serve to divert a portion of the light pulse emitted by light source 451 to a reference aperture 455 via optical fiber 462. Pulse modulator 468 may also wavelength-shift the light pulse so that it matches a wavelength-shifted exit signal of the light pulse that encountered voxel 433 while ultrasonic signal 117 was focused on voxel 433. In the illustrated embodiment, the energy meter is configured to measure the light pulse emitted by light source 451 before the light source encounters the pulse modulator 468. In some embodiments, energy meter 467 may be optically coupled to measure the light pulse downstream of pulse modulator 468 (after the light pulse encounters pulse modulator 468). Illumination aperture 454 is configured to receive the light pulse and emit the light pulse into medium 430.

While ultrasonic signal 117 is focused on voxel 433, emission 452 of the light pulse scatters in medium 430 and a portion of the emission 452 encounters voxel 433. In FIG. 4B, the wavelength-shifted portion of the illumination emission 452 is illustrated as shifted signal 443. Being influenced by ultrasonic signal 117, shifted imaging signal 443 has a different wavelength (lambda-two) than illumination emission 452 (lambda-one).

System 400 receives (at least a portion of) shifted signal 443. An input optic 447 may optionally be included in system 400. Input optic 447 may receive shifted signal 443 and guide the shifted signal 443 to be incident on image pixel array 470. In one embodiment, input optic 447 is configured to filter out an angled portion of the shifted signal 443.

Still referring to FIG. 4B, reference aperture 455 may optionally be configured to receive (at least a portion of) the light pulse emitted by light source 451 via optical fiber 462. Pulse modulator 468 may be driven to wavelength-shift the portion of the light pulse that propagates through optical fiber 462 so that the portion of the light pulse received by reference aperture 455 is lambda-two wavelength that matches the wavelength of wavelength-shifted exit signal 443. In other embodiments, reference aperture 455 may receive lambda-two wavelength light from a different light source than light source 451. The lambda-two wavelength reference wavefront 457 interferes with the incoming shifted signal 443 and image pixel array 470 captures the interference pattern generated by reference wavefront 457 interfering with exit signal 443. Reference director optic 456 in optical structure 480 may direct the lambda-two wavelength reference light to image pixel array 470 as a substantially uniform infrared reference wavefront 457.

Optionally, second energy meter 477 is optically coupled to measure an energy level of reference wavefront 457, in FIG. 4B. Second energy meter 477 generates reference energy level data of the measured energy level of reference wavefront 457 and provides the reference energy level data to logic 401 via communication channel X6, in the illustrated embodiment. Second energy meter 477 may be optically coupled to measure reference wavefront 457 in optical fiber 462, as in the illustrated embodiment. If reference wavefront 457 is generated by a discrete component such as a laser diode, second energy meter 477 may be coupled to the emission aperture of the discrete component. Processing logic 401 may synchronize the measurement of reference wavefront 457 with the emission of a light pulse from light source 451 via communication channels X3 and X6. Second energy meter 477 may include a photodiode or beam camera and function similarly to energy meter 467.

Shifted signal 443 may encounter input optic 447 and optical structure 480 prior to becoming incident upon image pixel array 470. The shifted signal 443 interferes with infrared reference wavefront 457 and image pixel array 470 captures an infrared image of the interference between shifted signal 443 and infrared reference wavefront 457. In one embodiment, reference director optic 456 is configured to deliver the infrared reference wavefront 457 to the image pixel array 470 at an angle to a pixel plane of the image pixel array 470. Processing logic 401 is coupled to initiate the image capture by image pixel array 470 via output X5, in the illustrated embodiment. Logic 401 is also coupled to receive the captured image from the image pixel array 470. Logic 401 may be configured to generate a composite image of diffuse medium 430 that includes captured images corresponding to different voxels of the diffuse medium.

A bandpass optical filter may be included in optical structure 480 or optic 447 to block out light signals that are not lambda-two wavelengths. A linear polarizer may also be included in optical structure 480 or optic 447 to polarize shifted signal 443 to have the same polarization orientation as infrared reference wavefront 457.

Figure 5:
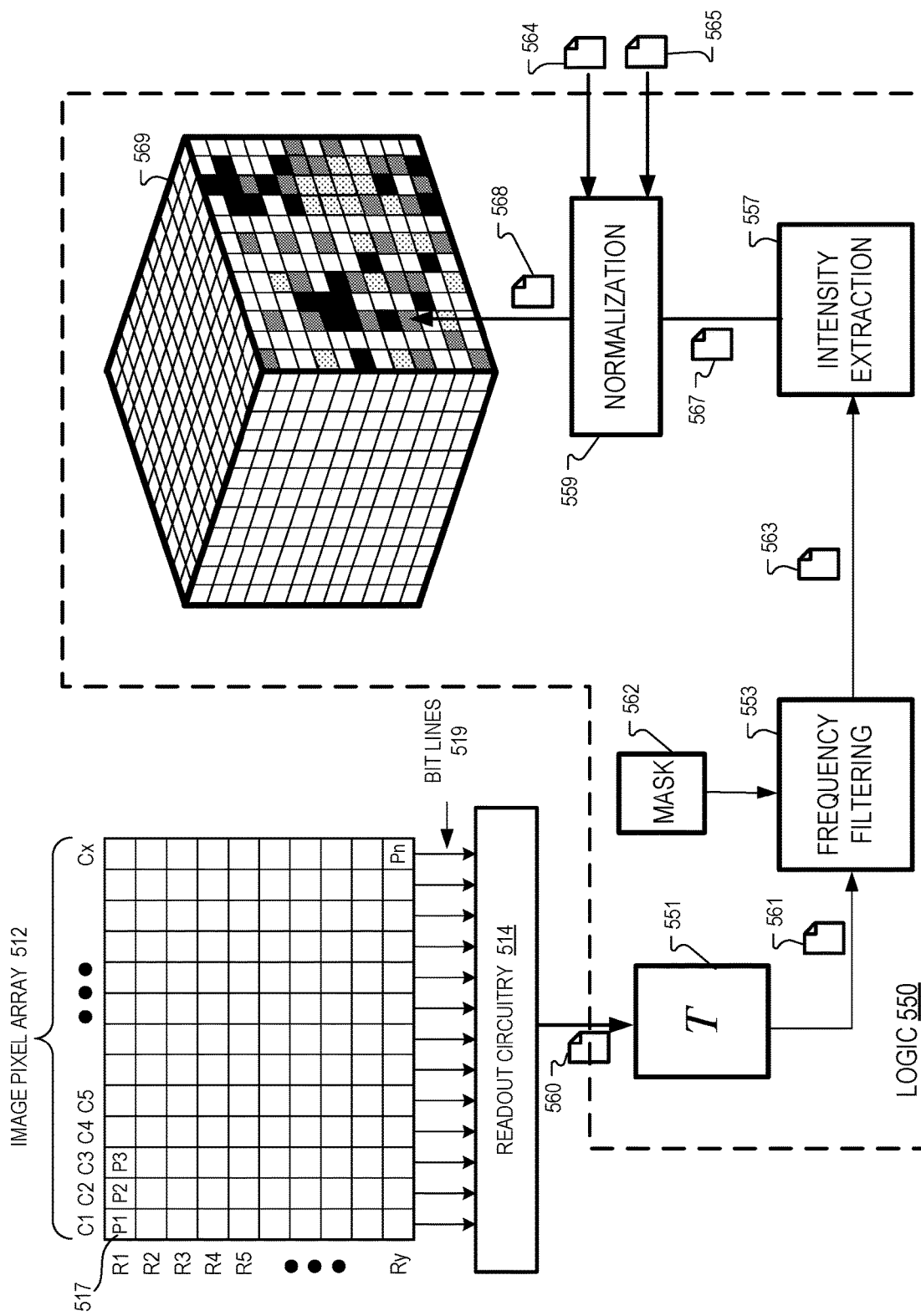
FIG. 5 illustrates an image pixel array coupled to example processing logic, in accordance with an embodiment of the disclosure.

FIG. 5 illustrates an image pixel array 512 coupled to example processing logic 550, in accordance with an embodiment of the disclosure. Processing logic 550 may be included in processing logic 401, in some embodiments. Image pixel array 512 includes image pixels 517 arranged in integer number x columns and integer number y rows. Readout circuitry 514 is coupled to read the signal value from each image pixels 517 via bitlines 519. Image pixel array 512 may be a complementary metal-oxide-semiconductor (CMOS) image pixel array. Image pixel array 512 may be an example of image pixel array 470 and be included in an image sensor.

Transform engine 551 in logic 550 is coupled to receive exit signal data 560 from readout circuitry 514, in FIG. 5. Exit signal data 560 may include an image including the interference pattern generated by shifted exit signal 443 interfering with reference wavefront 457. In some embodiments, transform engine 551 may be configured to receive exit signal data 560 from processing logic 401. Transform engine 551 generates a frequency domain image 561 by performing a Transform operation on an image included in exit signal data 560 received from readout circuitry 514. In one embodiment, the Transform operation includes a Fourier transform. In one embodiment, the Transform operation includes a discrete cosine transform.

Frequency filtering engine 553 is coupled to receive the frequency domain image 561 from Transform engine 551 and also coupled to receive mask 562. Frequency filtering engine 553 is configured to multiply the frequency domain infrared image 561 with the mask 562 to generate a filtered frequency domain image 563. Mask 562 is designed to isolate the frequency of the shifted signal 443 for further processing. Mask 562 may include a matrix that includes '1' values for the portion of the frequency domain image 561 that corresponds to the lambda-two wavelength of shifted signal 443 and '0' values for other portions of the frequency domain image 561. In one embodiment, mask 562 is a two-dimensional Gaussian filter.

Intensity extraction engine 557 is coupled to receive the filtered frequency domain image 563 and configured to extract intensity data 567 from the filtered frequency domain image 563. In one embodiment, generating the intensity data 567 includes averaging intensity values of the filtered frequency domain image 563. In an embodiment where a Fourier transform is used as the transform operation in Transform engine 551, the Fourier coefficients are extracted from filtered frequency domain image 563 and a sum of the logarithm of the absolute value of the Fourier coefficients is calculated. The sum is then used as intensity data 567.

Normalization logic 559 receives intensity data 567 and energy level data 565. Energy level data 565 may be provided by energy meter 467. Energy level data 565 may include one or more measurements of the intensity of the light pulse that was emitted from light source 451. Normalization logic 559 generates normalized intensity data 568 by normalizing the intensity data 567 with the energy level data 565. The normalization process used to generate normalized intensity data 568 may be linear normalization or non-linear normalization. Generating normalized intensity data in a linear process may include generating a normalization factor given by dividing a pre-determined baseline intensity value by the energy level data 565. The intensity data 567 may be multiplied by the normalization factor to generate the normalized intensity data 568.

In some embodiments, normalization logic 559 also receives reference energy level data 564. Reference energy level data 564 may be provided by second energy meter 477. Reference energy level data 564 may include one or more measurements of the intensity of reference wavefront 457. Normalization logic 559 may be further configured to generate the normalized intensity data by normalizing the exit signal data with the reference energy level data 564 (in addition to using energy level data 565 in the normalization process). In one embodiment, a first normalization value of the measured energy level data is determined and a second normalization value of the reference energy level data is determined. The product of the first normalization value and the second normalization value is squared and then multiplied by the intensity data 567 to generate normalized intensity data 568.

Logic 550 incorporates the normalized intensity data 568 as a voxel value in a composite image 569. Composite image 569 is illustrated as a three-dimensional image in FIG. 5 and may be a three-dimensional image of diffuse medium. As described in this disclosure, the system 400 may raster scan through diffuse medium 430 (focusing on different voxels) to generate a three-dimensional image of diffuse medium using a plurality of images corresponding to a plurality of energy level data 565 associated with the light pulse used to generate the respective image.

Figure 6:
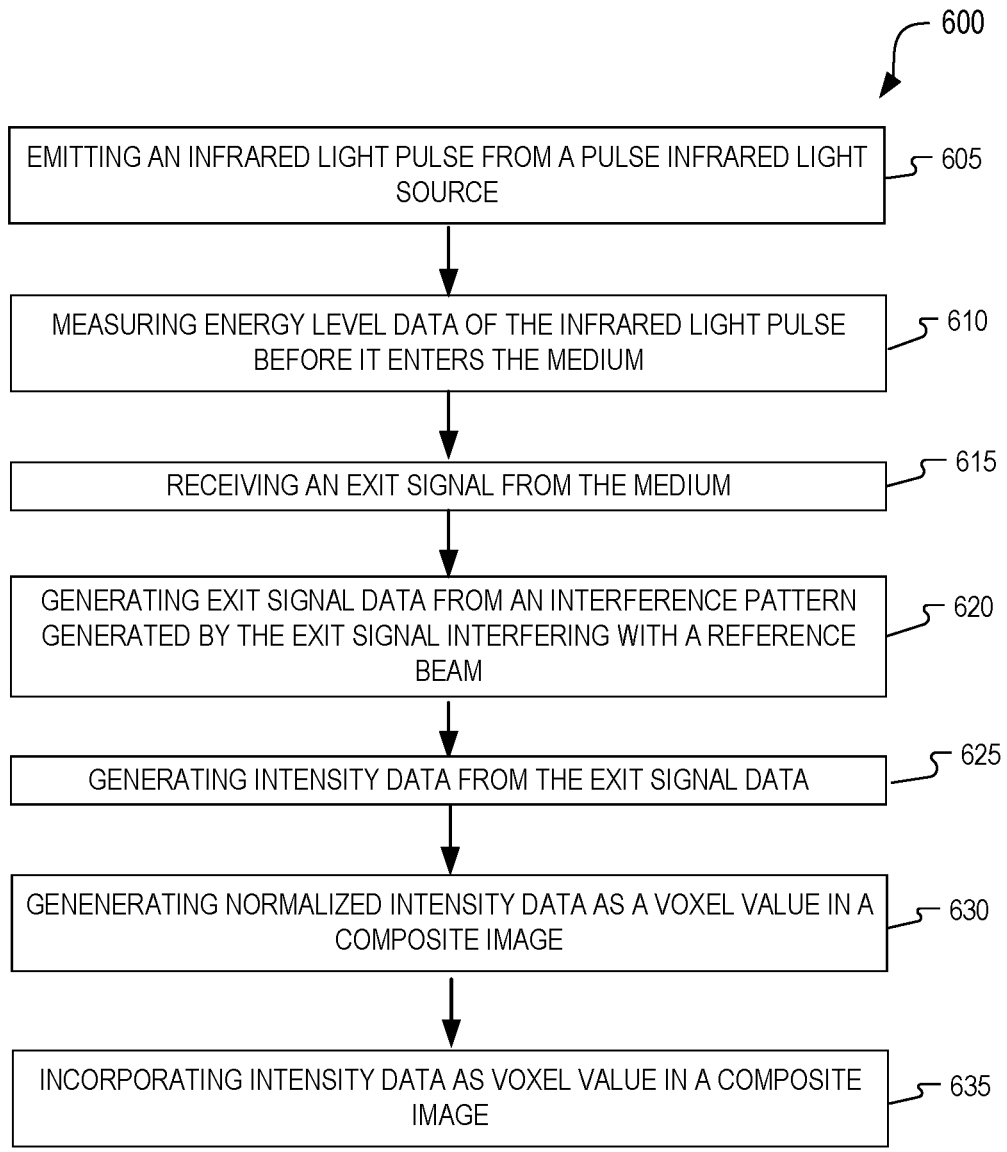
FIG. 6 illustrates an example flow chart of a process of optical imaging with pulse measurement, in accordance with an embodiment of the disclosure.

FIG. 6 illustrates an example flow chart of a process 600 of optical imaging with pulse measurement, in accordance with an embodiment of the disclosure. The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel. Processing logic 401 may execute the operations of process 600, for example.

In process block 605, an infrared light pulse is emitted from a pulsed infrared light source into a medium. The medium may be a diffuse medium such as tissue, for example.

In process block 610, energy level data (e.g. 565) of the infrared light pulse is measured before the infrared light pulse enters the medium. The energy level data may be measured by energy meter 467, for example. In one embodiment, measuring energy level data of the infrared light pulse includes measuring a plurality of light intensity measurements of the infrared light pulse over a time period. The time period may be from time t1 to t5, in FIG. 7. The time period may be over a pulse width of the infrared light pulse. In one embodiment, measuring the energy level data of the infrared light pulse includes calculating an area under an intensity curve formed by the plurality of light intensity measurements.

In process block 615, an exit signal is received from the medium. The exit signal is a portion of the infrared light pulse exiting the medium. The exit signal may be wavelength-shifted by an ultrasonic signal (e.g. 117) focused on a particular voxel of the medium.

In process block 620, exit signal data is generated from an interference pattern generated by the exit signal (e.g. 443) interfering with a reference wavefront (e.g. reference wavefront 457). The exit signal data may include an image of the interference pattern. Generating the exit signal data may include capturing an image of the interference pattern of the exit signal interfering with the reference wavefront.

In process block 625, intensity data (e.g. 567) is generated from the exit signal data. In some embodiments, generating the intensity data may further include generating a frequency domain image by performing a transform operation on the image, generating a filtered frequency domain image by applying a mask to the frequency domain image, and generating the intensity data from the filtered frequency domain image.

In process block 630, normalized intensity data (e.g. 568) is generated by normalizing the intensity data with the energy level data. In one embodiment, generating the normalized intensity data includes dividing a pre-determined baseline intensity value by the energy level data and multiplying the intensity data by the normalization factor.

In process block 635, the normalized intensity data is incorporated as a voxel value in a composite image (e.g. 569). The composite image may be of the medium and include a plurality of voxel values corresponding to different voxels of the medium.

Process 600 may also include measuring reference energy level data (e.g. 564) of a reference wavefront (e.g. 457) and generating the normalized intensity data also includes normalizing the intensity data with the reference energy level data.

Process 600 may also include emitting the reference wavefront to interfere with the exit signal. The reference wavefront may be the same wavelength as the exit signal.

Process 600 may also include activating an ultrasonic emitter to focus an ultrasonic signal on a voxel of the medium while illuminating the image sensor with the reference wavefront where the voxel value of the composite image is associated with the voxel of the medium.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Communication channels described in this disclosure may include wired or wireless communications utilizing IEEE 802.11 protocols, BlueTooth, SPI (Serial Peripheral Interface), I$^2$C (Inter-Integrated Circuit), USB (Universal Serial Port), CAN (Controller Area Network), cellular data protocols (e.g. 3G, 4G, LTE, 5G), or otherwise The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An imaging device comprising:
   a light source configured to emit a light pulse, wherein the light pulse is visible light or infrared light;
   an illumination aperture configured to receive the light pulse and emit the light pulse into a medium;
   an energy meter optically coupled to measure energy level data of the light pulse;
   an image sensor optically coupled to receive an exit signal from the medium and generate exit signal data based on the exit signal interfering with a reference wavefront, wherein the exit signal is a portion of the light pulse exiting the medium, and wherein the reference wavefront is generated by a reference wavefront generator; and
   normalization logic configured to receive the energy level data from the energy meter and configured to receive intensity data derived from the exit signal data from the image sensor, wherein the normalization logic is configured to generate normalized intensity data by normalizing the exit signal data with the energy level data.

2. The imaging device of claim 1 further comprising:
a second energy meter optically coupled to measure reference energy level data of the reference wavefront, wherein the normalization logic is further configured to generate the normalized intensity data by normalizing the exit signal data with the reference energy level data.

3. The imaging device of claim 1, wherein the normalized intensity data is incorporated into a composite image as a voxel value.

4. The imaging device of claim 1, wherein the light source is a pulsed laser and the light pulse is an infrared light pulse.

5. The imaging device of claim 1 further comprising:
an optical fiber configured to carry the light pulse to the illumination aperture, wherein the energy meter is optically coupled to optical fiber to measure the light pulse.

6. The imaging device of claim 1, wherein the energy level data includes a plurality of light intensity measurements over a time period.

7. The imaging device of claim 1 further comprising:
a pulse modulator configured to modulate the light pulse, wherein the energy meter is configured to measure the light pulse before the light pulse encounters the pulse modulator.

8. The imaging device of claim 1 further comprising:
a pulse modulator configured to modulate the light pulse, wherein the energy meter is configured to measure the light pulse after the light pulse is modulated by the pulse modulator.

9. The imaging device of claim 1, wherein the energy meter includes a photodiode or a beam camera.

10. The imaging device of claim 1, wherein the exit signal data includes an image.

11. A computer-implemented method of generating an infrared composite image, the method comprising:
emitting an infrared light pulse from a pulsed infrared light source into a medium;
measuring energy level data of the infrared light pulse before it enters the medium;
receiving an exit signal from the medium, wherein the exit signal is a portion of the infrared light pulse exiting the medium;
generating exit signal data from an interference pattern generated by the exit signal interfering with a reference wavefront generated by a reference wavefront generator;
generating intensity data from the exit signal data;
generating normalized intensity data by normalizing the intensity data with the energy level data; and
incorporating the normalized intensity data as a voxel value in a composite image, wherein the composite image is of the medium.

12. The method of claim 11 further comprising:
measuring reference energy level data of the reference wavefront, wherein generating the normalized intensity data also includes normalizing the intensity data with the reference energy level data.

13. The method of claim 11 further comprising:
emitting the reference wavefront to interfere with the exit signal, wherein the reference wavefront is of a same wavelength as the exit signal.

14. The method of claim 13, wherein generating the exit signal data includes capturing an image of an interference pattern of the exit signal interfering with the reference wavefront, and wherein the exit signal data includes the image captured by an image pixel array.

15. The method of claim 14, wherein generating the intensity data also includes:
generating a frequency domain image by performing a transform operation on the image;
generating a filtered frequency domain image by applying a mask to the frequency domain image; and
generating the intensity data from the filtered frequency domain image.

16. The method of claim 13 further comprising:
activating an ultrasonic emitter to focus an ultrasonic signal on a voxel of the medium while illuminating the image sensor with the reference wavefront, wherein the voxel value of the composite image is associated with the voxel of the medium.

17. The method of claim 16, wherein measuring energy level data of the infrared light pulse includes calculating an area under an intensity curve formed by a plurality of light intensity measurements.

18. The method of claim 11, wherein measuring energy level data of the infrared light pulse includes measuring, with a beam camera, a spatial beam shape of the infrared light pulse in space.

19. The method of claim 11, wherein generating the normalized intensity data includes generating a normalization factor by dividing a pre-determined baseline intensity value by the energy level data and multiplying the intensity data by the normalization factor.

20. A device comprising:
an infrared pulsed laser configured to emit an infrared laser pulse into tissue;
an energy meter optically coupled to measure energy level data of the infrared laser pulse before it enters the tissue;
an image sensor configured to capture an image of an interference pattern generated by an exit signal interfering with a reference wavefront generated by a reference wavefront generator, wherein the exit signal is a portion of the infrared laser pulse exiting the tissue; and
logic coupled to generate normalized intensity data in response to receiving the energy level data and the image.

* * * * *